United States Patent
McAlister

(10) Patent No.: US 10,130,508 B2
(45) Date of Patent: Nov. 20, 2018

(54) SYSTEM FOR POSITIONING TEMPERATURE CONTROL ELEMENT

(71) Applicant: Dennis McAlister, Cumming, GA (US)

(72) Inventor: Dennis McAlister, Cumming, GA (US)

( * ) Notice: Subject to any disclaimer, the term of this patent is extended or adjusted under 35 U.S.C. 154(b) by 364 days.

(21) Appl. No.: 15/067,154

(22) Filed: Mar. 10, 2016

(65) Prior Publication Data

US 2016/0262927 A1    Sep. 15, 2016

Related U.S. Application Data

(60) Provisional application No. 62/131,241, filed on Mar. 10, 2015.

(51) Int. Cl.
*A61F 7/02* (2006.01)
*A45C 13/10* (2006.01)
*A61F 7/00* (2006.01)
*A61F 7/03* (2006.01)

(52) U.S. Cl.
CPC ............... *A61F 7/02* (2013.01); *A45C 13/10* (2013.01); *A61F 7/007* (2013.01); *A61F 7/03* (2013.01); *A45C 2013/1015* (2013.01); *A61F 2007/023* (2013.01); *A61F 2007/0228* (2013.01); *A61F 2007/0231* (2013.01); *A61F 2007/0246* (2013.01); *A61F 2007/0249* (2013.01)

(58) Field of Classification Search
CPC ..... A61F 7/02–7/03; A61F 7/007; A61F 7/10; A61F 2007/0228; A45C 13/10; A45C 2013/1015; A45C 13/12; A45C 13/1076
See application file for complete search history.

(56) References Cited

U.S. PATENT DOCUMENTS

| | | | | |
|---|---|---|---|---|
| 5,020,536 A | * | 6/1991 | Keen | A61F 7/103 607/109 |
| 5,215,080 A | * | 6/1993 | Thomas | A61F 7/10 607/112 |
| 5,716,388 A | * | 2/1998 | Petelle | A61F 7/02 126/204 |
| 6,589,272 B1 | * | 7/2003 | Sheikh | A61F 7/02 607/108 |
| 6,945,988 B1 | * | 9/2005 | Jones | A61F 7/10 607/108 |
| 2006/0058860 A1 | * | 3/2006 | Ferdinand | A61F 7/10 607/108 |
| 2008/0040839 A1 | * | 2/2008 | Gordon | A41D 13/0053 2/455 |

(Continued)

*Primary Examiner* — Kristen Matter

(57) ABSTRACT

Described herein is a pouch or strap system for holding a temperature control element (i.e., hot/cold element). The system described herein may include multiple straps that may be retained and/or interconnected such that the system may position a temperature control element at various parts of the body. The system may include a central pouch encompassed by a first panel and a second panel, wherein the first panel has a higher thermal resistance than the thermal resistance of the second panel. The system may include a first couple of straps attached to and extending away from the central pouch, each of the first couple of straps including a single quick-release buckle component, and a second couple of straps attached to and extending away from the central pouch, wherein each strap of the second couple of straps includes two quick-release buckle components.

20 Claims, 5 Drawing Sheets

(56) References Cited

U.S. PATENT DOCUMENTS

| | | | |
|---|---|---|---|
| 2010/0057173 A1* | 3/2010 | Leavitt | A61F 7/10 607/114 |
| 2011/0066218 A1* | 3/2011 | Geibel | A61F 7/02 607/112 |
| 2011/0077573 A1* | 3/2011 | Pain | A61D 9/00 602/63 |
| 2014/0058486 A1* | 2/2014 | Moore, Jr. | A61F 7/10 607/112 |

* cited by examiner

SYSTEM FOR POSITIONING TEMPERATURE CONTROL ELEMENT

CROSS REFERENCE TO RELATED APPLICATION

This application is a non-provisional application claiming the benefit of U.S. Provisional Application Ser. No. 62/131,241, entitled "System for Positioning Temperature Control Element," which was filed on Mar. 10, 2015, and is incorporated herein by reference in its entirety.

TECHNICAL FIELD

This disclosure relates to a wrap for holding a temperature control element.

BACKGROUND

Temperature control elements are used for various therapeutic purposes. Temperature control elements such as hot or cold packs may be used to apply a desired temperature to a certain body part. In some instances, a user may desire to place a hot/cold element into contact with various body parts. Currently, there are no systems or apparatuses for positioning a hot/cold element to apply temperature at various locations on the body.

BRIEF DESCRIPTION OF THE DRAWINGS

Like reference numbers and designations in the various drawings indicate like elements.

DETAILED DESCRIPTION

Figure 1:
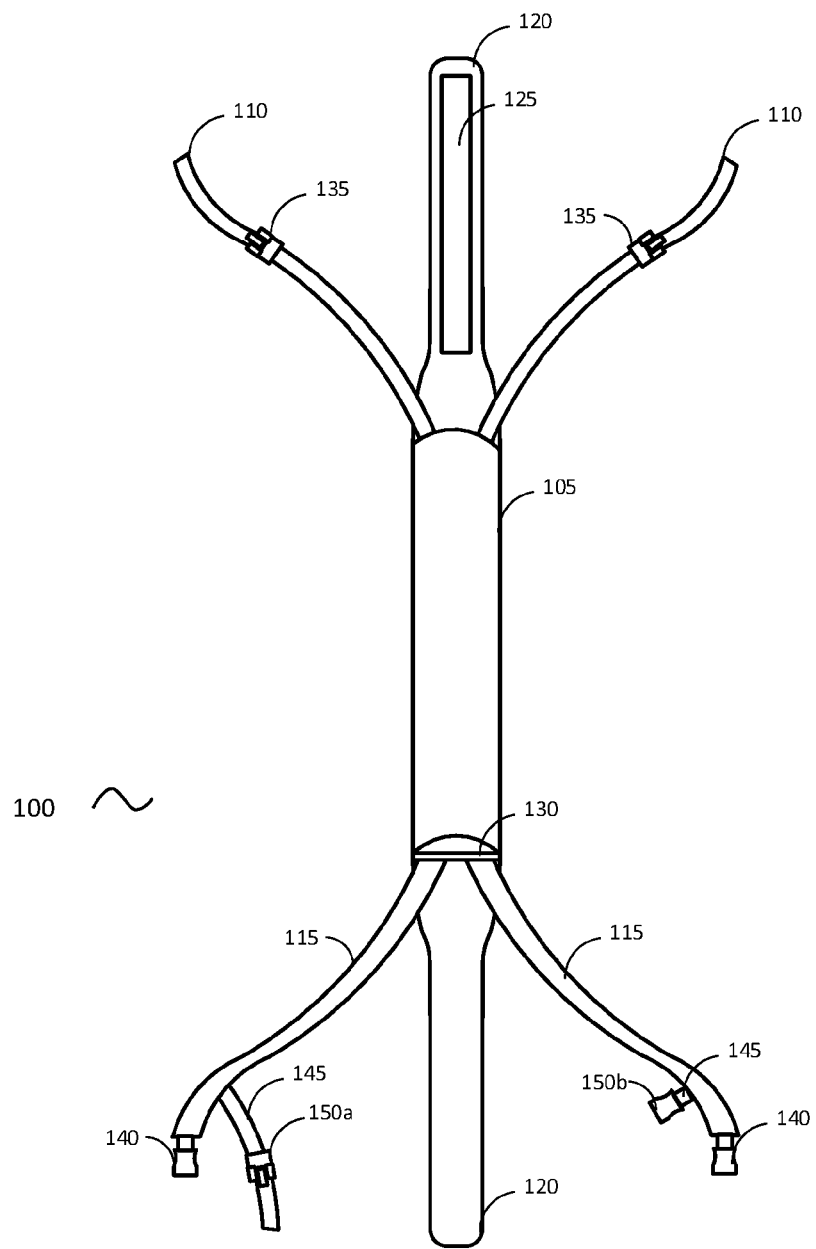
FIG. 1 is a front view of a system for positioning a temperature control element.

As a preliminary matter, it will be readily understood by those persons skilled in the art that the present invention is susceptible of broad utility and application. Many methods, embodiments, and adaptations of the present invention other than those herein described, as well as many variations, modifications, and equivalent arrangements will be apparent from or reasonably suggested by the present invention and the following description thereof without departing from the substance or scope of the present invention. Accordingly, while the present invention has been described herein in detail in relation to preferred embodiments, it is to be understood that this disclosure is only illustrative and exemplary of the present invention and is made merely for the purpose of providing an enabling disclosure of the invention. The following disclosure is not intended nor is to be construed to limit the present invention or otherwise to exclude any such other embodiments, adaptations, variations, modifications and equivalent arrangements.

Described herein is a pouch or strap system for holding a temperature control element (i.e., hot/cold element). The system described herein may include multiple straps that may be retained and/or interconnected such that the system may position a temperature control element at various parts of the body. The system may include a central pouch encompassed by a first panel and a second panel, wherein the first panel has a higher thermal resistance than the thermal resistance of the second panel. The system may include a first couple of straps attached to and extending away from the central pouch, each of the first couple of straps including a single quick-release buckle component, and a second couple of straps attached to and extending away from the central pouch, wherein each strap of the second couple of straps includes two quick-release buckle components.

An embodiment of the invention described herein may include a temperature control element pouch comprising: (a) a central section; (b) a first tapered strap attached at one end to the central section and extending away from the central section; (c) a second tapered strap attached at one end to the central section and extending away from the central section; (d) a first strap attached at one end to a first side of the central section, wherein the first strap comprises a quick release buckle component; (e) a second strap attached at one end to the first side of the central section, wherein the second strap comprises a quick release buckle component; (f) a third strap attached at one end to a second side of the central section, wherein the third strap comprises: (i) a quick release buckle component; and (ii) a secondary strap attached at one end to the third strap, the secondary strap comprising a quick release buckle component; and (g) a fourth strap attached at one end to the second side of the central section, wherein the fourth strap comprises two quick release buckle components.

According to an embodiment of the invention described herein, the central section comprises an insulated shell, and the lateral edges of the insulated shell are detached.

According to an embodiment of the invention described herein, the lateral edges of the insulated shell comprise hook and loop fastener components.

According to an embodiment of the invention described herein, the central section comprises a compartment encompassed by an inner panel and an outer panel, and the outer panel has a higher thermal resistance than the thermal resistance of the inner panel.

According to an embodiment of the invention described herein, the compartment is dimensioned so as to hold a heating or cooling element.

According to an embodiment of the invention described herein, the central section further comprises a secondary compartment having detached lateral edges with hook and loop fastener components, wherein the first strap, the second strap, the third strap, and the fourth strap are attached to the central section at a location within the secondary compartment.

According to an embodiment of the invention described herein, the position of the quick release buckle component along the third strap is adjustable.

An embodiment of the invention described herein may include a temperature control element pouch comprising: (a) a central section; (b) a first strap attached at one end to a first side of the central section, wherein the first strap comprises a quick release buckle component; (c) a second strap attached at one end to the first side of the central section, wherein the second strap comprises a quick release buckle component; (d) a third strap attached at one end to a second side of the central section, wherein the third strap comprises: (i) a quick release buckle component; and (ii) a secondary strap attached at one end to the third strap, the secondary strap comprising a quick release buckle component; and (e) a fourth strap attached at one end to the second side of the central section, wherein the fourth strap comprises two quick release buckle components.

According to an embodiment of the invention described herein, the central section comprises an insulated shell, and the lateral edges of the insulated shell are detached.

According to an embodiment of the invention described herein, the lateral edges of the insulated shell comprise hook and loop fastener components.

According to an embodiment of the invention described herein, the central section comprises a compartment encompassed by an inner panel and an outer panel, and the outer panel has a higher thermal resistance than the thermal resistance of the inner panel.

According to an embodiment of the invention described herein, the compartment is dimensioned so as to hold a heating or cooling element.

According to an embodiment of the invention described herein, the central section further comprises a secondary compartment having detached lateral edges with hook and loop fastener components, wherein the first strap, the second strap, the third strap, and the fourth strap are attached to the central section at a location within the secondary compartment.

According to an embodiment of the invention described herein, the position of the quick release buckle component along the third strap is adjustable.

An embodiment of the invention described herein may include a temperature control element pouch comprising a temperature control element pouch comprising: (a) a central section; (b) a first strap attached at one end to a first side of the central section, wherein the first strap comprises a quick release buckle component; (c) a second strap attached at one end to the first side of the central section, wherein the second strap comprises a quick release buckle component; (d) a third strap attached at one end to a second side of the central section, wherein the third strap comprises two quick release buckle components; and (e) a fourth strap attached at one end to the second side of the central section, wherein the fourth strap comprises two quick release buckle components.

According to an embodiment of the invention described herein, the central section comprises an insulated shell, and the lateral edges of the insulated shell are detached.

According to an embodiment of the invention described herein, the central section comprises a compartment encompassed by an inner panel and an outer panel, and the outer panel has a higher thermal resistance than the thermal resistance of the inner panel.

According to an embodiment of the invention described herein, the compartment is dimensioned so as to hold a heating or cooling element.

According to an embodiment of the invention described herein, the central section further comprises a secondary compartment having detached lateral edges with hook and loop fastener components, wherein the first strap, the second strap, the third strap, and the fourth strap are attached to the central section at a location within the secondary compartment.

According to an embodiment of the invention described herein, the position of the quick release buckle component along the third strap is adjustable.

FIG. 1 is a front view of a system for positioning a temperature control element. The system for positioning a temperature control element may be referred to herein as a multi-purpose hot/cold wrap 100. The multi-purpose hot/cold wrap 100 may include, a strap pouch 105, two or more single-connector straps 110, and two or more double-connector straps 115.

The multi-purpose hot/cold wrap 100 may have a center section and tapered straps 120 extending away from the center section. One of the tapered straps 120 may be covered with a hook-and-loop fabric. For example, the tapered edge 120 may be covered with a loop component 125 of a hook-and-loop fastening system. It should be understood that the tapered straps 120 may be of various lengths such that the tapered straps 120 may be wrapped around a body in various ways. In embodiments, one or more of the tapered straps 120 can be adjustable.

In embodiments, the strap pouch 105 may include a front panel (i.e., piece of fabric or other material) covering the rectangular center section of the multi-purpose hot/cold wrap, wherein the top and bottom edges of the front panel are affixed to the hot/cold wrap (e.g., the top and bottom edges may be sewn to the wrap). A hook-and-loop fastener system 130 may be attached along the interior edge of each side of the front panel, and an opposing component of the hook-and-loop fastener may be affixed to the wrap. Both sides of the strap pouch may be opened and closed such that the two single-connector straps 110 and the two double-connector straps 115 may be retained within the strap pouch 105. It should be understood that any other means may be used to allow the sides of the strap pouch 105 to be opened and closed (e.g., zipper system, magnets, buttons, etc.).

In embodiments, each of the two or more single-connector straps 110 may be attached to the multi-purpose hot/cold wrap 100 at the same edge of the central section (i.e., within the strap pouch 105). Each single-connector strap 110 may include a side-release buckle component 135 (e.g., a male side-release buckle component or a female side-release buckle component). The single-connector strap 110 may be passed through the side-release buckle component 135 such that the side-release buckle component 135 may slide along the length of the single-connector strap 110.

In embodiments, each of the two or more double-connector straps 115 may be attached to the multi-purpose hot/cold wrap 100 at the same edge of the central section (i.e., within the strap pouch 105), and the double-connector straps 115 may be attached at the edge of the central section opposite of the edge at which the single-connector straps 110 are attached.

A side-release buckle component 140 (e.g., a male side-release buckle component or a female side-release buckle component) may be affixed at the end of each double-connector strap 115. For example, the side-release buckle component 140 affixed at the end of each double-connector strap 115 may be the side-release buckle component that mates with the side-release buckle component 135 attached to the single-connector straps 110.

In embodiments, a secondary strap 145 may be attached to each double-connector strap 115, and the secondary strap 145 may extend away from the associated double-connector strap 115 at or near a perpendicular angle. A side-release buckle component 150a-b (e.g., a male side-release buckle component or a female side-release buckle component) may be attached to each secondary strap 145, and the secondary strap 145 may be passed through the side-release buckle component 150a-b such that the side-release buckle component 150a-b may slide along the length of the secondary strap 145. For example, the side-release buckle component 150*a-b* attached to the secondary strap 145 may be a buckle component that mates with the side-release buckle component affixed to the end of each single-connector strap 110 or double-connector strap 115. In embodiments, the two side-release buckle components 150*a-b* attached to the secondary straps 145 may be opposing components (i.e., the side-release buckle component 150*a* of one secondary strap 145 can mate with the side-release buckle component 150*b* of the other secondary strap 145). A side-release buckle component 150*b* of one of the secondary straps 145 may be affixed at the end of the secondary strap 145.

In embodiments, one of the secondary straps 145 may be longer than the other secondary strap 145. For example, the secondary strap 145 to which the side-release buckle component 150*a* is affixed may be longer than the secondary strap 145 to which the side-release buckle component 150*b* is affixed. The side-release buckle component 150*a* may slide along the length of the longer secondary strap 145.

In embodiments, the strap pouch 105 may be dimensioned such that one or more single-connector straps 110 and/or one or more double-connector straps 115 may be retained within the strap pouch 105. The strap pouch 105 and the tapered straps 120 may be so dimensioned (e.g., length and width dimensions), such that the tapered straps 120 may be folded into and retained within the strap pouch 105.

Figure 2:
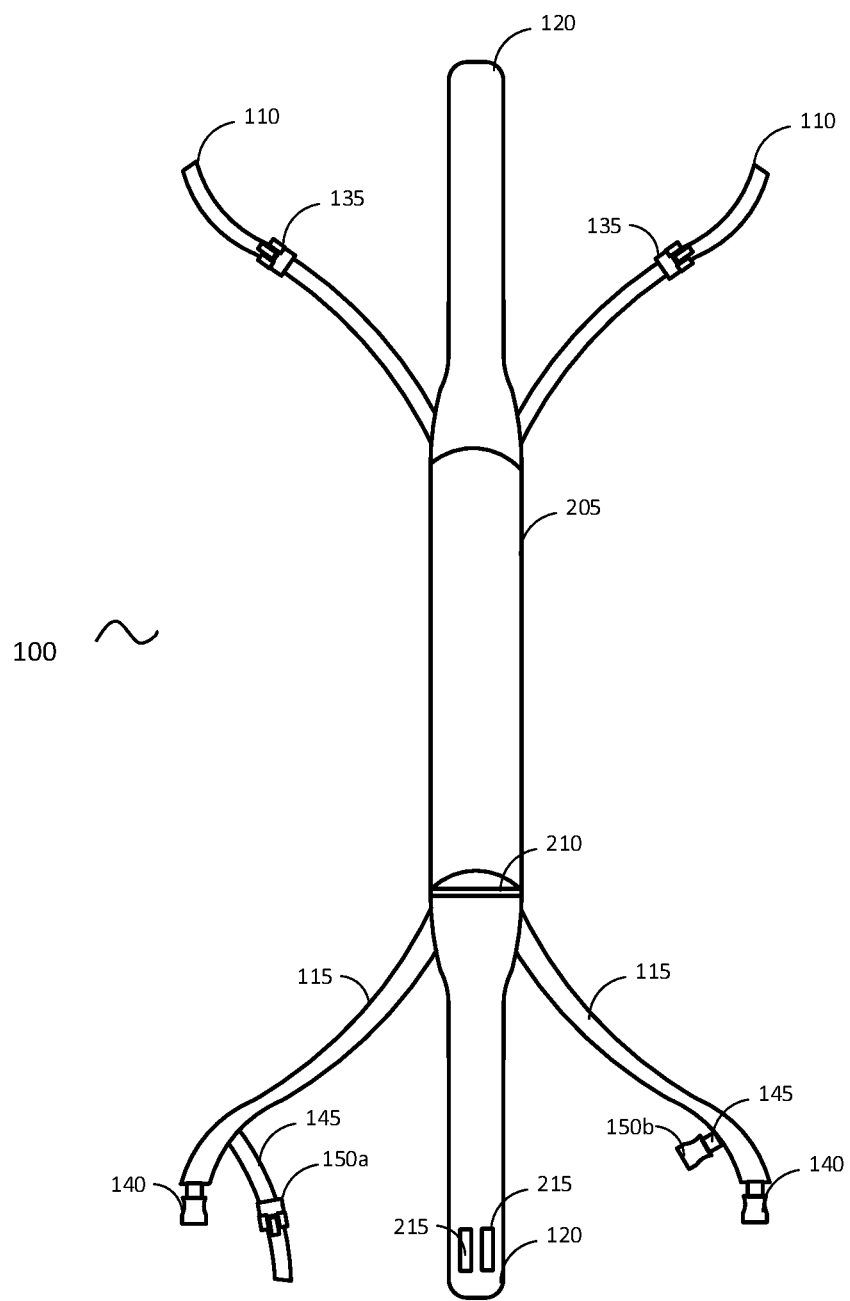
FIG. 2 is a rear view of a system for positioning a temperature control element.

FIG. 2 is a rear view of a system for positioning a temperature control element. In embodiments, a center section at the rear of the hot/cold wrap 100 may include a hot/cold element pouch 205. The hot/cold element pouch 205 may include a rear panel (i.e., piece of fabric) covering the rectangular center section of the multi-purpose hot/cold wrap 100, wherein the top and bottom edges of the rear panel are affixed to the hot/cold wrap 100 (e.g., the top and bottom edges may be sewn to the wrap). A hook-and-loop fastener system 210 may be attached along the interior edge of each side of the rear panel, and an opposing component of the hook-and-loop fastener may be affixed to the wrap 100. Both sides of the hot/cold element pouch 205 may be opened and closed such that a hot/cold element may be retained within the hot/cold element pouch 205. It should be understood that any other means may be used to allow the sides of the hot/cold element pouch 205 to be opened and closed (e.g., zipper system, magnets, buttons, etc.).

In embodiments, the interior wall of the hot/cold element pouch 205 may be made of a material that serves to reduce temperature dissipation from the hot/cold element through the interior wall. The exterior wall of the hot/cold element pouch 205 may be made of a material that facilitates temperature dissipation or heat transfer from the hot/cold element to an intended target through the exterior wall. For example, the exterior wall of the hot/cold element pouch 205 may be made of a mesh material.

In embodiments, the rear of the tapered edge 120 opposite of the tapered strap covered with a hook-and-loop fabric at the front may include one or more strips of hook-and-loop fabric 215 that mates with the hook-and-loop fabric at the front of the opposing tapered strap.

The single-connector straps 110 including the side-release buckle components 135 and the double-connector straps 115 including the secondary straps 145 and side-release buckle components 140 and 150*a-b* may be attached to the side of the wrap 100 opposing the hot/cold element pouch 205.

Figure 3:
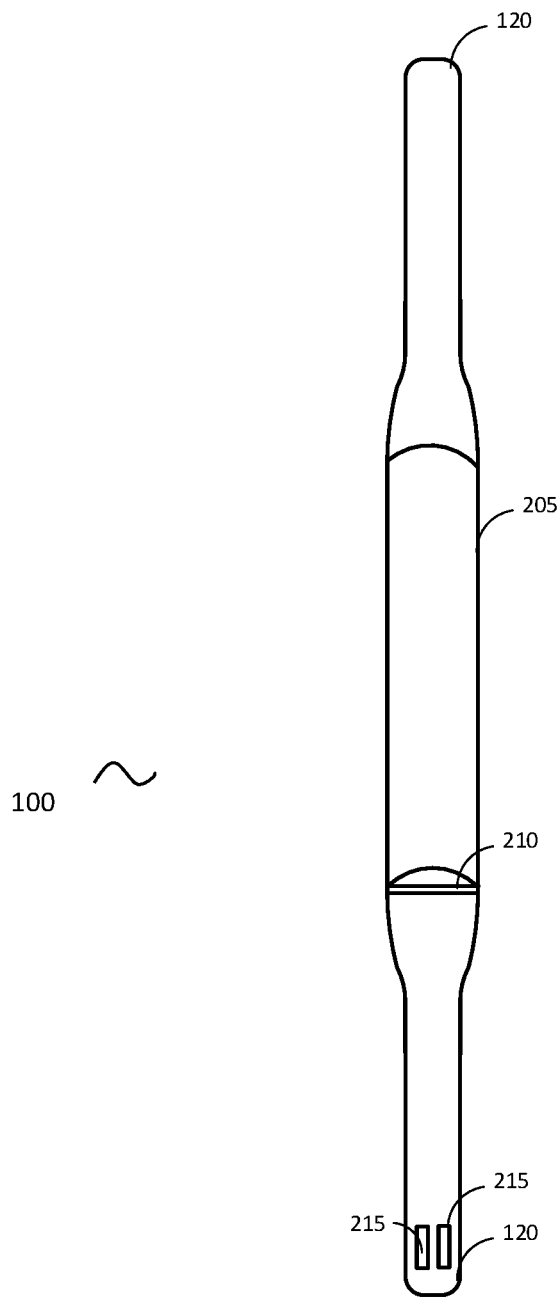
FIG. 3 is a rear view of a system for positioning a temperature control element, wherein the single-connector straps and double-connector straps are retained within a front pouch.

FIG. 3 is a rear view of a system for positioning a temperature control element, wherein the single-connector straps and double-connector straps are retained within a front pouch. In embodiments, the single-connector straps 110 of FIG. 1 and the double-connector straps 115 of FIG. 1 may be retained within a front pouch of the wrap 100. A heating or cooling element (e.g., a chemical or electrical heating or cooling element) may be retained within the hot/cold element pouch 205 via the hook-and-loop fastener system 210. The hook-and-loop fabric strips 215 and the loop component 125 of FIG. 1 of the tapered straps 120 may be used to hold the wrap 100 in place with the heating or cooling element placed at a desired location of a body. It should be understood that a hook-and-loop fastener system 210 may be located at one or both sides of the hot/cold element pouch 205.

Figure 4:
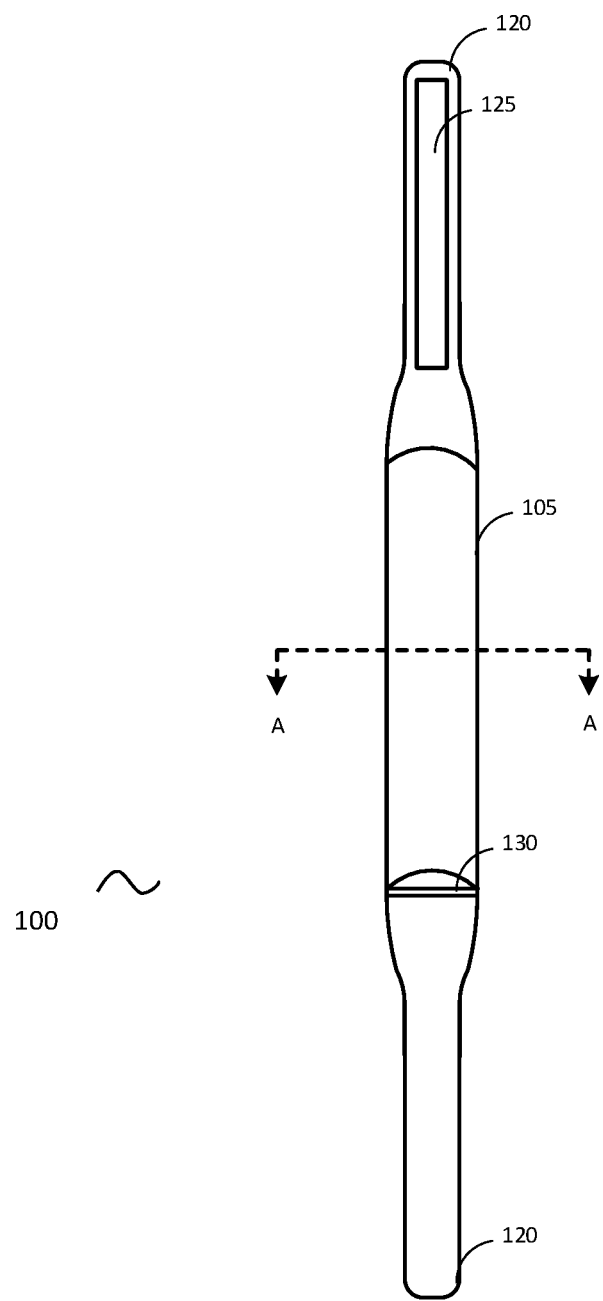
FIG. 4 is a front view of a system for positioning a temperature control element, wherein the single-connector straps and double-connector straps are retained within a front pouch.

FIG. 4 is a front view of a system for positioning a temperature control element, wherein the single-connector straps and double-connector straps are retained within a front pouch. In embodiments, the single-connector straps 110 of FIG. 1 and the double-connector straps 115 of FIG. 1 may be retained within the strap pouch 105 of the wrap 100. The hook-and-loop fastener system 130 may allow the strap pouch 105 to be opened and closed to place and retain the single-connector straps 110 and double-connector straps 115 within the strap pouch 105. It should be understood that a hook-and-loop fastener system 130 may be located at one or both sides of the strap pouch 105.

A heating or cooling element (e.g., a chemical or electrical heating or cooling element) may be retained within the hot/cold element pouch 205 of FIG. 2 via the hook-and-loop fastener system 210 of FIG. 2. The hook-and-loop fabric strips 215 of FIG. 2 and the loop component 125 of the tapered straps 120 may be used to hold the wrap 100 in place with the heating or cooling element placed at a desired location of a body.

Figure 5:
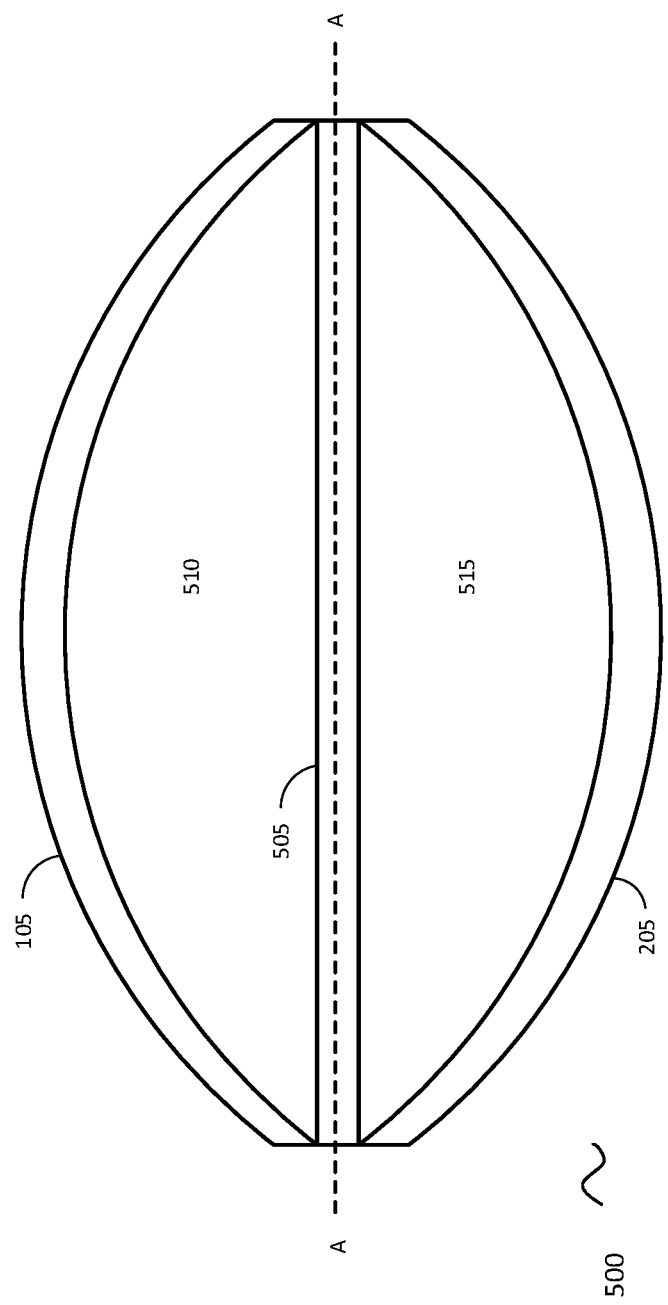
FIG. 5 is a cross-sectional side view of a system for positioning a temperature control element.

FIG. 5 is a cross-sectional side view 500 of a system for positioning a temperature control element. The cross-sectional side view 500 shows a cross-sectional view corresponding with the cross-section view lines (A-A) depicted in FIG. 4. In embodiments, the central section of the wrap 100 of FIG. 1 may include a central panel 505, a strap pouch 105, and a hot/cold element pouch 205. The central panel 505 may separate a strap void 510 and a temperature control element void 515 and may extend away from the central section of the wrap as the tapered straps 120 of FIG. 1. The strap pouch 105 and the hot/cold element pouch 205 may create an insulated shell encompassing the strap void 510 and the temperature control element void 515.

The surfaces of the central panel 505 and the strap pouch 105 (e.g., a front panel) may encompass a strap void 510. The single-connector straps 110 of FIG. 1 and the double-connector straps 115 of FIG. 1 may be retained within the strap pouch 105.

The surfaces of the central panel 505 and the hot/cold element pouch 205 may encompass a temperature control element void 515. A heating or cooling element (e.g., a chemical or electrical heating or cooling element) may be retained within the temperature control element void 515. In embodiments, the front panel (i.e., the strap pouch 105) may have a higher thermal resistance than the rear panel (i.e., the hot/cold element pouch 205. For example, the front panel may be thicker than the rear panel and/or the front panel may be made of a material having a higher thermal resistance than the material making up the rear panel (e.g., the rear panel may be a mesh or other breathable material). With the rear panel having a lower thermal resistance than the front panel, heat may be transferred from a hot/cold element within the temperature control element void 515 to a body or from a body to a hot/cold element within the temperature control element void 515 through the rear panel. Moreover, heat loss or gain from the hot/cold element within the temperature control element void 515 to an outside environment through the front panel may be minimized with the higher thermal resistance of the front panel. In embodiments, the central panel 505 may provide additional thermal resistance to prevent heat loss or gain from the hot/cold element within the temperature control element void 515 to an outside environment.

It should be understood that where side-release buckle components are referred to herein, the buckle components may be replaced by quick-release buckle components and other means for attaching two components of the system.

In embodiments, the various straps of the hot/cold wrap 100 may be used to orient a temperature control element at different positions of a body. The plurality of straps may be oriented such that the temperature control element is located at a back or chest/torso area. The plurality of straps may be oriented such that the temperature control element may be located at a back or waist/torso area. The plurality of straps may be oriented such that the temperature control element is located at a shoulder.

It should be understood that the side-release buckles described herein may be replaced by other mechanisms for connecting two or more components of the strap system.

What is claimed is:

1. A temperature control element pouch comprising:
   a central section;
   a first tapered strap attached at one end to the central section and extending away from the central section;
   a second tapered strap attached at one end to the central section and extending away from the central section;
   a first strap attached at one end to a first side of the central section, wherein the first strap comprises a quick release buckle component;
   a second strap attached at one end to the first side of the central section, wherein the second strap comprises a quick release buckle component;
   a third strap attached at one end to a second side of the central section, wherein the third strap comprises:
     a quick release buckle component; and
     a secondary strap attached at one end to the third strap, the secondary strap comprising a quick release buckle component; and
   a fourth strap attached at one end to the second side of the central section, wherein the fourth strap comprises two quick release buckle components.

2. The temperature control element pouch of claim 1, wherein the central section comprises an insulated shell, and wherein one or more lateral edges of the insulated shell are detached.

3. The temperature control element pouch of claim 2, wherein the lateral edges of the insulated shell comprise hook and loop fastener components.

4. The temperature control element pouch of claim 1, wherein the central section comprises a compartment encompassed by an inner panel and an outer panel, and wherein the outer panel has a higher thermal resistance than a thermal resistance of the inner panel.

5. The temperature control element pouch of claim 4, wherein the compartment is dimensioned so as to hold a heating or cooling element.

6. The temperature control element pouch of claim 5, wherein the central section further comprises a secondary compartment having detached lateral edges with hook and loop fastener components, wherein the first strap, the second strap, the third strap, and the fourth strap are attached to the central section at a location within the secondary compartment.

7. The temperature control element pouch of claim 5, wherein a position of the quick release buckle component on the third strap along the third strap is adjustable.

8. A temperature control element pouch comprising:
   a central section;
   a first strap attached at one end to a first side of the central section, wherein the first strap comprises a quick release buckle component;
   a second strap attached at one end to the first side of the central section, wherein the second strap comprises a quick release buckle component;
   a third strap attached at one end to a second side of the central section, wherein the third strap comprises:
     a quick release buckle component; and
     a secondary strap attached at one end to the third strap, the secondary strap comprising a quick release buckle component; and
   a fourth strap attached at one end to the second side of the central section, wherein the fourth strap comprises two quick release buckle components.

9. The temperature control element pouch of claim 8, wherein the central section comprises an insulated shell, and wherein one or more lateral edges of the insulated shell are detached.

10. The temperature control element pouch of claim 9, wherein the lateral edges of the insulated shell comprise hook and loop fastener components.

11. The temperature control element pouch of claim 8, wherein the central section comprises a compartment encompassed by an inner panel and an outer panel, and wherein the outer panel has a higher thermal resistance than the thermal resistance of the inner panel.

12. The temperature control element pouch of claim 11, wherein the compartment is dimensioned so as to hold a heating or cooling element.

13. The temperature control element pouch of claim 12, wherein the central section further comprises a secondary compartment having detached lateral edges with hook and loop fastener components, wherein the first strap, the second strap, the third strap, and the fourth strap are attached to the central section at a location within the secondary compartment.

14. The temperature control element pouch of claim 12, wherein a position of the quick release buckle component on the third strap along the third strap is adjustable.

15. A temperature control element pouch comprising:
   a central section;
   a first strap attached at one end to a first side of the central section, wherein the first strap comprises a quick release buckle component;
   a second strap attached at one end to the first side of the central section, wherein the second strap comprises a quick release buckle component;
   a third strap attached at one end to a second side of the central section, wherein the third strap comprises two quick release buckle components; and
   a fourth strap attached at one end to the second side of the central section, wherein the fourth strap comprises two quick release buckle components.

16. The temperature control element pouch of claim 15, wherein the central section comprises an insulated shell, and wherein one or more lateral edges of the insulated shell are detached.

17. The temperature control element pouch of claim 15, wherein the central section comprises a compartment encompassed by an inner panel and an outer panel, and wherein the outer panel has a higher thermal resistance than the thermal resistance of the inner panel.

18. The temperature control element pouch of claim 17, wherein the compartment is dimensioned so as to hold a heating or cooling element.

19. The temperature control element pouch of claim 18, wherein the central section further comprises a secondary compartment having detached lateral edges with hook and loop fastener components, wherein the first strap, the second strap, the third strap, and the fourth strap are attached to the central section at a location within the secondary compartment.

20. The temperature control element pouch of claim 18, wherein a position of the quick release buckle component on the third strap along the third strap is adjustable.

* * * * *